United States Patent [19]

Lambert

[11] Patent Number: 4,497,798
[45] Date of Patent: Feb. 5, 1985

[54] APPETITE SUPPRESSANT

[76] Inventor: Teresa C. Lambert, R.D. #4, Red Lion, Pa. 17356

[21] Appl. No.: 506,004

[22] Filed: Jun. 20, 1983

[51] Int. Cl.³ ...................... A61K 33/14; A61K 31/19
[52] U.S. Cl. .................................... 424/153; 514/557
[58] Field of Search ............................... 424/153, 317

[56] References Cited

U.S. PATENT DOCUMENTS

| | | | |
|---|---|---|---|
| 3,337,404 | 8/1967 | Polli et al. | 424/153 |
| 3,970,750 | 7/1976 | Brockemeyer et al. | 424/153 |
| 4,042,684 | 8/1977 | Kahm | 424/153 |
| 4,154,814 | 5/1979 | Hand et al. | 424/48 |
| 4,259,323 | 3/1981 | Ranucci | 424/153 |
| 4,312,856 | 1/1982 | Korduner et al. | 424/153 |
| 4,322,407 | 3/1982 | Ko | 424/153 |
| 4,352,791 | 10/1982 | Zaffaroni | 424/153 |

OTHER PUBLICATIONS

Chem. Abst. 66, 84901(t), (1967)—Boissier et al.
Chem. Abst. 83, 146250(s), (1975)—McNeff.
Chem. Abst. 96, 216423(v), (1982)—Li et al.

Primary Examiner—Douglas W. Robinson
Attorney, Agent, or Firm—Samuel M. Learned, Jr.

[57] ABSTRACT

A palatable liquid dispersed potassium compound dissolution for human oral ingestion to physiologically induce an appetite suppressive response being for use thereof at times of hunger pang sensation and as an appetite satiant substance and method to aid in accomplishing weight control and reduction procedures by dampening the impulse to eat.

1 Claim, No Drawings

APPETITE SUPPRESSANT

BACKGROUND OF THE INVENTION

The present invention relates and details the unexpected discovery that potassium functions as an appetite suppressant, and that certain potassium compound compositions have been found suitable for employment as such when prepared in the liquid dissolved and diluted state in preferred and alternate formulation embodiment versions and used by the method hereof in solute form for human oral ingestion, wherein both the substance and method of employment are for purposes of accomplishing the physiological elimination or substantial reduction of hunger pang sensations and thereby aid in repressing between-meal impulsive eating and appetite suppression at times of normal and habitual meal taking.

It is known that the potassium cation role and importance in intracellular fluids as an ion exchange medium in effecting essential physiological processes such as the transmission of nerve impulses is of fundamental importance, the need for which is in turn essential in maintaining human health. In the foregoing respect, potassium based formulations with additive components in solution form have been employed to beneficial advantage as electrolyte drink substances used for rapid effect replenishing of water and essential electrolyte constituents lost from human body fluids during periods of sustained physical activity, an exemplary teaching of which substance is set forth in U.S. Pat. No. 4,322,407 to Ko dated Mar. 30, 1982, for a potassium chloride component compounding that is reconstituted with water to provide an electrolyte drink of the type described.

Other disclosures which teach the bioactive electrolyte properties of potassium chloride component compounds are respectively set forth in U.S. Pat. No. 4,154,814 to Hand et al dated May 15, 1979, therein disclosing a therapeutic chewing gum containing both sodium chloride and potassium chloride which when orally utilized functions to maintain body fluid saline solution content at an electrolyte level at which ingested fluids are optimally assimilated into the blood stream, and U.S. Pat. No. 4,042,684 to Kahm dated Aug. 16, 1977, disclosing a dietetic beverage comprising an aqueous solution of sugar with both sodium and potassium chloride and flavor enhancing free citric acid to be taken for supplementing sugar and essential salts that are depleted during engagement in vigorous physical activity.

Even though potassium is an essential and necessary element for proper and balanced human organism bioactive functioning, it is nonetheless known that in the salt compound forms thereof, and in particular as that of potassium chloride which in general is the most convenient and available and economical potassium salt for pharmaceutical uses, it is capable of causing and creating certain gastro-intestinal side effect problems characteristically associated with the oral ingestive employment of potassium compound salts including nausea, vomiting, diarrhea, and/or gastric and intestinal ulceration. There are, however, various ways in which to avoid or minimize the detrimental side effect problems above-noted the simplest of which is to administer potassium compound salt on a sparing schedule only as needed in the minimum dose necessary to effect the desired physiological response and to administer that minimum effective dose amount in a liquid dissolved and diluted form to thereby further avoid high concentration direct contact exposure of the gastro-intestinal walls to a potassium compound tablet or loose powder administered dose which tends to create a site of gastro-intestinal mucosa lining irritation due to the localized contact exposure thereof to a high concentration dissolving point of the potassium compound or salt solids.

Another way to enhance the safe pharmaceutical uses of orally ingested potassium salts is to buffer the formulation with other components which do not interfere with the potassium bioactive function but do neutralize the irritating effects thereof such as made known in that teaching for potassium replacement therapy set forth in U.S. Pat. No. 4,352,791 to Zaffaroni et al dated Oct. 5, 1982, therein disclosing the mixing of salicylic acid with potassium chloride to provide a potassium compound substance for oral ingestive use which avoids the gastro-intestinal problems such as ulceration otherwise associated with the use of potassium chloride. Another such teaching is set forth in U.S. Pat. No. 4,259,323 to Ranucci dated Mar. 31, 1981, therein disclosing an oral ingestive water-in-oil emulsion of potassium chloride solution which minimizes the potential intestinal irritation problems and also efficiently masks the otherwise objectionable potassium chloride saline taste.

In the foregoing regard, potassium salt taste problems may also be covered or reduced by the employment to good advantage of various sour fruit flavors, such as the inclusion of a citric acid component as in the Kahm teaching cited supra.

The instant invention for an orally ingested liquid dissolved and diluted potassium compound appetite suppressant, which may in the formulations thereof include various optional ingredients in addition to sour fruit flavoring additives or alternately sweeteners as flavoring agents, such as for example color additives and the like, has by experiment been found to produce the appetite satient effect as an apparent consequence of the bioactive physiological function of that available potassium in the dose amounts administered by the method specified, and while it is not presently known how or why the potassium compound solutions of instant invention yield the desired appetite suppressant result, and although some of the formulations of instant invention are somewhat similar in the component constituents and content thereof to some of those potassium compound based formulations as recited in certain of the prior art teachings noted for use either as electrolyte beverages or in potassium therapy procedures, the instant invention is distinguishable from said earlier teachings in one or more ways in that the present invention has new and useful advantages, applications, and improvements in the art and method of appetite suppression procedure and technique not heretofore known.

SUMMARY OF THE INVENTION

It is the principal object of the present invention to provide a potassium compound appetite suppressant composition and method of use which when orally ingested in the manner of use described physiologically operates to safely and effectively curb appetite pang discomfort so as to reduce the frequency and amount of impulsive eating between meals, and reduce the amount of food taken at times of regular meals, thereby functioning as a substance and technique for employment in weight reduction and control procedures.

Consistent with the foregoing principal object, it is further an object hereof to provide an appetite suppressant composition in the form of a liquid dissolved and dispersed dilution, or in a tablet or granular form which may be readily converted thereto, thereby facilitating the ease of oral ingestive taking and reducing substantially any hazards of intestinal irritation or gastro-intestinal complications otherwise likely to result from oral ingestive use of more concentrated potassium salt compound forms.

It is a further object of the instant invention to provide an appetite suppressant method of use which also reduces even further any likelihood of side effect hazards due to intestinal irritation or gastro-intestinal complications otherwise generally attendant to less conservative potassium compound oral ingestive administration technique.

It is also an object of the instant invention to provide a potassium compound appetite suppressant in liquid form which does not have the characteristic unpleasant saline taste.

Yet another object of the instant invention is to provide an appetite suppressant composition comprised of relatively inexpensive and readily available constituents safe for human oral ingestion both singularly and in combination, namely a potassium compound component, a flavoring agent, and a suitable liquid medium for the dissolving and dispersing and dilution thereof.

It is an additional object of the instant invention that the particular potassium compound component, in combination with other appetite suppressant formulation components such as various flavoring agents and the like, be chemically compatable and stable when dissolved into solution in the liquid medium dispersing and diluting oral ingestion vehicle.

Another object of the instant invention is to provide an appetite suppressant of the type described which has no ingestion after taste consequent from or associated with the liquid medium formulation.

Further objects and advantages of the instant invention will become apparent to those skilled in the art upon an examination of the following detailed description of the invention.

DETAILED DESCRIPTION OF THE INVENTION

The present invention relates to a palatible potassium compound liquid dispersed solution for human oral ingestion to physiologically induce an appetite suppression sensation for employment thereof as a substance to aid in weight control and reduction procedures.

The potassium compound appetite suppressant formulations and examples hereinafter reflect applicant's personal preferances as regards taste variances in respectively determining that which constitutes a palatible liquid dissolved product for oral ingestion and are not, therefore, to be regarded as restrictive since each was developed in view of effectively masking the otherwise objectionable saline taste sensation normally associated with compounds of potassium when the same are incorporated in sufficient quantity into the composition formulation to bioactively produce the observed appetite suppressing physiological effect while at the same time limiting the potassium compound concentration thereof to a dispersed and diluted level in the liquid medium dose at a strength typically below that amount which might otherwise create known side effect hazards such as stomach irritation and the like from an increased ingestion of potassium salts.

While it is not presently known precisely how or why the potassium compound compositions of instant invention yield the desired and observed appetite suppressant result, it is possible that such result can be explained by either one or a combination of the following two theories, neither of which, singularly or in combination, however, is to be considered in any way as limiting. It is known that potassium salts, and in particular potassium chloride, functions as a body electrolyte and improves and effects the transmission of physiological impulses through the central nervous system in a manner not unlike that of the flow of current in an electrical conductor. According to one theory the electrolytic composition hereof through the potassium cation component gratifyingly stimulates by such transmission mechanism the hunger sensation neurological sensory perception and thereby renders the appetite or hunger impulse satisfied.

Another theory, however, explains the appetite satient effect upon a physiological phenomenon whereby it is possible the composition causes a change of the bioelectric transmission circuit of the central nervous system thereby effecting its impulse transmitting abilities as a consequence of the potassium cation concentration imbalance resultant from ingestion of the bioactive electrolytic solution composition hereof.

It should be understood, however, that there is no definitive evidence at hand which either proves or disproves one or both of the aforementioned theories and, accordingly, the same are mentioned here only for completeness and potentially accurate explanation purposes.

Further, it is to be understood that because of differing individual tastes, physiological reactions, and tolerance levels to oral ingestion of potassium compound formulations, and in particular to potassium salt solution compositions, as evidenced by the use of such for treatment of other conditions as previously described, the formulations hereof may be adjusted to accommodate the potassium compound concentration in solution to levels of personal preference and still obtain the desired appetite suppressant result observed substantially without any detrimental side effect consequences as aforesaid. And, depending on a number of factors, being of primary consideration the desired duration of appetite suppression as balanced against possible side effect consequences as above described, and that which is considered to be an acceptably palatable oral ingestion solution, the essential ingredients in terms of composition and content may be within the ranges as follows and still produce the observed results:

| Ingredient | Range of Amount |
| --- | --- |
| Potassium Compound | 100 to 1,000 mEq of K |
| Flavoring Agent | 0 to 5 Teaspoons |
| Liquid | 3 to 16 Fluid Ounces |

NOTE:
mEq - Milliequivalent of Potassium, being the grams of potassium contained in one milliliter of a normal solution.

The essential ingredients of the appetite suppressant composition according to the present invention, in the preferred embodiment thereof by way of composition and content, is as follows:

| Ingredient | Preferable Amount |
| --- | --- |
| Potassium Compound | 330 mEq of K |
| Flavoring Agent | ¼ Teaspoon |

-continued

| Ingredient | Preferable Amount |
| --- | --- |
| Liquid | 6 Fluid Ounces |

The most suitable potassium compound form is that of a potassium salt, and of the various potassium salts either dry granular pharmaceutical grade potassium chloride or potassium citrate have both been found to be equally suitable and interchangeable as the potassium compound component in the content amount shown by the above-recited preferred embodiment formulation. In most cases the flavoring agent used was sugar primarily because of availability, economy, and chemical stability and compatability with the other of the formulation components. The liquid used for dissolving, dispersing, and diluting the potassium compound components with flavoring agents ranged from tap water to various commercially available fruit, vegetable, and citrus juices, and fruit/citrus juice mixtures as well as vegetable juice blends and dairy beverages.

Examples of specific appetite suppressant compositions in accordance with the foregoing as based on the preferred content embodiment therefor are as follows:

EXAMPLE I

The following ingredients are combined to provide a neutral flavored liquid dissolved and dispersed appetite suppressant beverage in accordance with the instant invention:

| Ingredient | Amount |
| --- | --- |
| Potassium Chloride | 1/12 Teaspoon |
| Sugar | ⅛ Teaspoon |
| Tap Water | 6 Fluid Ounces |

In the above example the potassium chloride amount is slowly added with constant stirring to the tap water at room temperature until dissolved after which the sugar is likewise slowly added with constant stirring until dissolved.

For effecting appetite suppression the resulting beverage as above prepared is orally ingested at times of hunger pang sensation or just prior to the time of habitual meal taking.

EXAMPLE II

This appetite suppressant beverage is prepared and taken in the same manner as above-described, except the active ingredient in this compounding in accordance with the instant invention is potassium citrate:

| Ingredient | Amount |
| --- | --- |
| Potassium Citrate | ⅛ Teaspoon |
| Sugar | ⅛ Teaspoon |
| Tap Water | 6 Fluid Ounces |

Variations on the foregoing specific appetite suppressant beverage compositions in accordance with the instant invention, likewise prepared and taken in the same manner as above-described include the following:

EXAMPLE III

| Ingredient | Amount |
| --- | --- |
| Potassium Chloride | 1/12 Teaspoon |
| Sugar | ⅛ Teaspoon |
| Fruit/Citrus Juice Mixture | 6 Fluid Ounces |

EXAMPLE IV

| Ingredient | Amount |
| --- | --- |
| Potassium Citrate | ⅛ Teaspoon |
| Sugar | ⅛ Teaspoon |
| Fruit/Citrus Juice Mixture | 6 Fluid Ounces |

EXAMPLE V

| Ingredient | Amount |
| --- | --- |
| Potassium Chloride | 1/12 Teaspoon |
| Sugar | ⅛ Teaspoon |
| Fruit Juice | 6 Fluid Ounces |

EXAMPLE VI

| Ingredient | Amount |
| --- | --- |
| Potassium Citrate | ⅛ Teaspoon |
| Sugar | ⅛ Teaspoon |
| Fruit Juice | 6 Fluid Ounces |

EXAMPLE VII

| Ingredient | Amount |
| --- | --- |
| Potassium Chloride | 1/12 Teaspoon |
| Sugar | ⅛ Teaspoon |
| Citrus Juice | 6 Fluid Ounces |

EXAMPLE VIII

| Ingredient | Amount |
| --- | --- |
| Potassium Citrate | ⅛ Teaspoon |
| Sugar | ⅛ Teaspoon |
| Citrus Juice | 6 Fluid Ounces |

EXAMPLE IX

| Ingredient | Amount |
| --- | --- |
| Potassium Chloride | 1/12 Teaspoon |
| Sugar | ⅛ Teaspoon |
| Vegetable Juice | 6 Fluid Ounces |

EXAMPLE X

| Ingredient | Amount |
| --- | --- |
| Potassium Citrate | ⅛ Teaspoon |
| Sugar | ⅛ Teaspoon |
| Vegetable Juice | 6 Fluid Ounces |

EXAMPLE XI

| Ingredient | Amount |
|---|---|
| Potassium Chloride | 1/12 Teaspoon |
| Sugar | ½ Teaspoon |
| Vegetable Juice Blend | 6 Fluid Ounces |

EXAMPLE XII

| Ingredient | Amount |
|---|---|
| Potassium Citrate | ¼ Teaspoon |
| Sugar | ½ Teaspoon |
| Vegetable Juice Blend | 6 Fluid Ounces |

EXAMPLE XIII

| Ingredient | Amount |
|---|---|
| Potassium Chloride | 1/12 Teaspoon |
| Sugar | ½ Teaspoon |
| Chocolate Milk | 6 Fluid Ounces |

EXAMPLE XIV

| Ingredient | Amount |
|---|---|
| Potassium Citrate | ¼ Teaspoon |
| Sugar | ½ Teaspoon |
| Chocolate Milk | 6 Fluid Ounces |

The appetite suppressant beverage in any of the foregoing formulation versions is orally ingested at times of hunger pang sensation and/or prior to habitual meal taking in order to realize the optimum satient effect thereof.

In all of the foregoing examples, where it may be appropriate and applicable, it is to be understood that the liquid component thereof may be prepared from the corresponding dry concentrate counterpart form by first reconstituting with water or milk and then employing the same for the dissolving, dispersing, and diluting medium as above described. Likewise, it is also to be understood that the corresponding dry concentrate counterpart form of the liquid component may be mixed with the potassium compound component and the flavoring agent component in dry concentrate form either as a powder or tablet and then reconstituted with either water or milk as appropriate.

While the invention has been described in terms of a preferred embodiment of composition components and content thereof, the person of skill in the art will appreciate that various substitutions, modifications, changes, and omissions may be made without departing from the spirit thereof. Accordingly, it is intended that the invention be limited solely by the scope of the following claims.

I claim:

1. A method for effecting appetite suppression utilizing an appetite suppressant beverage comprised of a compound of potassium combined with a flavoring agent compound together dissolved and diluted in a liquid medium, said beverage to be ingested orally by a human at times of hunger pang sensation for effecting extended duration physiological elimination thereof to thereby aid in repressing between-meal impulsive eating and appetite reduction at times of habitual meal taking.

* * * * *